US012773355B2

(12) United States Patent
Corrado

(10) Patent No.: US 12,773,355 B2
(45) Date of Patent: Oct. 27, 2026

(54) DEVICES, SYSTEMS, AND METHODS FOR USE IN CONNECTION WITH UMBILICAL HERNIAS

(71) Applicant: Cathlyn Corrado, Victor, NY (US)

(72) Inventor: Cathlyn Corrado, Victor, NY (US)

(73) Assignee: Neotech Products LLC, Valencia, CA (US)

(*) Notice: Subject to any disclaimer, the term of this patent is extended or adjusted under 35 U.S.C. 154(b) by 13 days.

(21) Appl. No.: 18/749,782

(22) Filed: Jun. 21, 2024

(65) Prior Publication Data

US 2024/0335333 A1 Oct. 10, 2024

Related U.S. Application Data

(63) Continuation of application No. 17/714,619, filed on Apr. 6, 2022, now abandoned.

(Continued)

(51) Int. Cl.

*A61F 13/14* (2006.01)
*A61F 13/00* (2024.01)

(52) U.S. Cl.

CPC ... *A61F 13/148* (2013.01); *A61F 2013/00119* (2013.01); *A61F 2013/0028* (2013.01)

(58) Field of Classification Search

CPC ........ A61F 15/008; A61F 2/0009; A61F 5/24; A61F 2013/00118; A61F 2013/0028; A61F 2013/00089; A61F 2013/00582; A61F 2013/1504; A61F 2013/15032; A61F 13/00; A61F 13/00021; A61F 13/14; A61F 13/148; A61F 13/0289; A61F 13/0259; A61F 13/0253; A61F 13/0246; A61F 13/023; A61F 13/02; A61F 13/493

(Continued)

(56) References Cited

U.S. PATENT DOCUMENTS

| | | | |
|---|---|---|---|
| 6,274,786 | B1 | 8/2001 | Heller |
| 8,742,196 | B2 | 6/2014 | Arbesman |

(Continued)

FOREIGN PATENT DOCUMENTS

| | | | |
|---|---|---|---|
| BR | PI0803182-7 A2 | 8/2010 | |
| CN | 102920549 A | 2/2013 | |

(Continued)

OTHER PUBLICATIONS

Boonkerd, C. and Limroongreungrat, W., Elastic therapeutic tape: do they have the same material properties?, J. Phys. Ther. Sci. 28: 1303-1306, 2016.

(Continued)

*Primary Examiner* — Caitlin A Carreiro

(74) *Attorney, Agent, or Firm* — Michael A. DiNardo; YK LAW LLP

(57) ABSTRACT

A device for treatment of an umbilical hernia includes a first section of flexible, elastic material including an adhesive layer on a rearward side thereof. The first section includes an opening therein dimensioned to encompass the umbilical. The device further includes a plurality of extending sections of flexible, elastic material attached to and extending from the first section. Each of the extending sections includes an adhesive layer on a rearward side thereof. The first section is less elastic than each of the plurality of extending sections.

20 Claims, 4 Drawing Sheets

Related U.S. Application Data

(60) Provisional application No. 63/171,664, filed on Apr. 7, 2021.

(58) Field of Classification Search
USPC ........ 128/96.1, 101.1, 887, 890; 604/385.09, 604/304, 307; 602/41, 54, 57, 58, 60, 61
See application file for complete search history.

(56) References Cited

U.S. PATENT DOCUMENTS

| | | | | |
|---|---|---|---|---|
| D743,566 | S | 11/2015 | Arbesman | |
| 2010/0016771 | A1 * | 1/2010 | Arbesman | A61F 13/066 602/5 |
| 2010/0298747 | A1 | 11/2010 | Quinn | |
| 2012/0232448 | A1 | 9/2012 | Wust | |
| 2017/0296391 | A1 * | 10/2017 | Kendall | A61F 13/0233 |

FOREIGN PATENT DOCUMENTS

| | | | |
|---|---|---|---|
| CN | 203609581 | U | 5/2014 |
| CN | 207871055 | U | 9/2018 |
| CN | 210228447 | U | 4/2020 |
| CN | 211460847 | U | 9/2020 |

OTHER PUBLICATIONS

De Ru, Ester et al., Taping Umbilicus Hernias in young children: presenting a novel non-compressive possibility, Clinic Notes from Poland and the Netherlands, Jun. 2018.
Kinesio Tex Gold Light flier, Light Touch, Feb. 25, 2021.
Mini x-Spiders, Small Athletic Tape, Spider Tech, Mar. 28, 2021, https://spidertech.com/us/mini-x-spiders.
Navel Compression Pack, Nichiban Co., Ltd, Mar. 8, 2021, https://www.nichiban.com/medical/navel_compression_pack/.
Tweet Figure, Temporary fix for my umbilical hernia blow out, Sep. 8, 2020.

* cited by examiner

DEVICES, SYSTEMS, AND METHODS FOR USE IN CONNECTION WITH UMBILICAL HERNIAS

CROSS-REFERENCE TO RELATED APPLICATIONS

This application is a continuation application of U.S. patent application Ser. No. 17/714,619, filed Apr. 6, 2022, which claims benefit of U.S. Provisional Patent Application Ser. No. 63/171,664, filed Apr. 7, 2021, the disclosures of which are incorporated herein by reference.

BACKGROUND

The following information is provided to assist the reader in understanding technologies disclosed below and the environment in which such technologies may typically be used. The terms used herein are not intended to be limited to any particular narrow interpretation unless clearly stated otherwise in this document. References set forth herein may facilitate understanding of the technologies or the background thereof. The disclosure of all references cited herein are incorporated by reference.

Umbilical hernias are one of the most common pediatric surgical conditions affecting 20-30% of infants during their first year of life. This number is even higher in those children who are born premature or have altered muscle tone. An umbilical hernia leaves the child with a gap in their core musculature through which their abdominal contents (intestines and fluid) will protrude. During a time of such significant growth and development, it is problematic that the suggested treatment for these types of hernias is a “wait and see” approach to see if the hernia closes before the child is 3 years old. At 3 years old, anesthesia and surgical correction becomes a safer option if a hernia has not closed by itself. As a result, it can be up to 3 years of worry for a parent, and months to years of development where the child’s core is weaker than it needs to be.

A number of studies address umbilical hernia with the use of elastic tape applied to the child’s abdomen. For example, Clinic Notes from Poland and the Netherlands describes a uniplanar and basic muscle approximation to improve appearance of umbilical hernias with elastic kinesiology tape that comes in a 2-inch width roll and is cut by each clinician. Nothing is pre-fabricated. Licensed and trained physical therapist, not parents, perform the applications of the kinesiology tape to the child’s abdomen.

A product from Kinesio Light includes a 2-inch or 1-inch roll of tape that each clinician can cut to use for a variety of reasons such as muscle activation, lymphedema control, or stability. Once again, nothing is prefabricated for infants. The product is sold as a roll and a clinician cuts and applies each length of tape. The tape is applied every three days.

Umbilical hernia belts are also available for use with infants that wrap circumferentially around the infant’s stomach to decrease protrusion of the hernia. However, such belts can impede the natural pattern of breathing, impede the natural movement, and can be uncomfortable. Moreover, umbilical hernia belts do not promote natural healing.

Adults also experience umbilical hernias. In general, umbilical hernias in adults are less likely heal on their own than umbilical hernias in infants. Umbilical hernias in adults typically grow larger over time and may require surgical repair. Umbilical hernias are, for example, common during pregnancy. Treatments for umbilical hernias in adults are limited.

SUMMARY

In one aspect, a device for treatment of an umbilical hernia includes a first section of flexible, elastic material including an adhesive layer on rearward side thereof. The first section includes an opening therein dimensioned to encompass the umbilical. The device further includes a plurality of extending sections of flexible, elastic material attached to and extending from the first section. Each of the plurality of extending sections includes an adhesive layer on a rearward side thereof. The first section is less elastic than each of the plurality of extending sections in a number of embodiments. The device may further include one or more removable backing sections or layers over the adhesive layer of the first section and over each of the plurality of extending sections.

In a number of embodiments, a first plurality of the extending sections extend from a first side of the first section and a second plurality of the extending sections extend from a second side of the first section. In a number of embodiments, the first plurality of extending sections and the second plurality of extending sections have a maximum elongation in the range of 25 to 150%, in the range of 25 to 100% or in the range of 50 to 100%. The maximum elongation of the first section is in the range of 15 to 85% less than the maximum elongation of the extending sections in a number of embodiments. In a number of embodiments, the first section has a thickness greater than each of the plurality of extending sections.

In a number of embodiments, kinesiology tape is used in the devices, systems, and method hereof. In a number of embodiments, the elastic materials used herein may have material properties that are similar to or mimic those of human skin. In general, the material properties of the elastic materials used in the devices, systems, and method hereof can vary over a relatively broad range while accomplishing the objects set forth herein. The material properties (for example, elasticity and maximum elongation) of each of the first section and the second section of device hereof may be predetermined at the time of manufacture.

In another aspect, a method of treating an umbilical hernia includes providing a preassembled device including a first section of flexible, elastic material which includes an adhesive layer on rearward side thereof. The first section also includes an opening therein dimensioned to encompass the umbilical. The preassembled device further includes a plurality of extending sections of flexible, elastic material attached to and extending from the first section. Each of the plurality of extending sections includes an adhesive layer on a rearward side thereof. The first section is less elastic than each of the plurality of extending sections. The first section of the preassembled device is applicable to the abdomen of an individual (for example, the abdomen of a child) having the umbilical hernia, and each of the plurality of extending sections of flexible, elastic material is applicable to the abdomen. In a number of embodiments, the first section is less elastic than each of the plurality of extending sections. The method may further include removing one or more removable backing layers or sections over the adhesive layer of the first section and over each of the plurality of extending sections before applying the first section and each of the plurality of extending sections to the patient.

As described above, in a number of embodiments, a first plurality of the extending sections extend from a first side of the first section and a second plurality of the extending sections extend from a second side of the first section. In a number of embodiments, the first plurality of extending sections and the second plurality of extending sections have a maximum elongation in the range of 25 to 150%, in the range of 25 to 100% or in the range of 50 to 100%. The maximum elongation of the first section is in the range of 15 to 85% less than the maximum elongation of the extending sections in a number of embodiments. In a number of embodiments, the first section has a thickness greater than each of the plurality of extending sections. A plurality of the devices may be provided.

In a further aspect, a kit includes a plurality of devices for treatment of an umbilical hernia which are prefabricated for application. Each of the devices includes a first section of flexible, elastic material comprising an adhesive layer on rearward side thereof. The first section includes an opening therein dimensioned to encompass the umbilical. Each device further includes a plurality of extending sections of flexible, elastic material attached to and extending from the first section. Each of the plurality of extending sections include an adhesive layer on a rearward side thereof. The first section is less elastic than each of the plurality of extending sections. Each of the devices may further include one or more removable backing sections or layers over the adhesive layer of the first section and over each of the plurality of extending sections.

As described above, in a number of embodiments, a first plurality of the extending sections extend from a first side of the first section of each device and a second plurality of the extending sections extend from a second side of the first section of each device. In a number of embodiments, the first plurality of extending sections and the second plurality of extending sections have a maximum elongation in the range of 25 to 150%, in the range of 25 to 100% or in the range of 50 to 100%. The maximum elongation of the first section of each device may, for example, be in the range of 15 to 85% less than the maximum elongation of the extending sections in a number of embodiments. In a number of embodiments, the first section of each device has a thickness greater than each of the plurality of extending sections.

The present devices, systems, and methods, along with the attributes and attendant advantages thereof, will best be appreciated and understood in view of the following detailed description taken in conjunction with the accompanying drawings.

DETAILED DESCRIPTION

Figure 1:
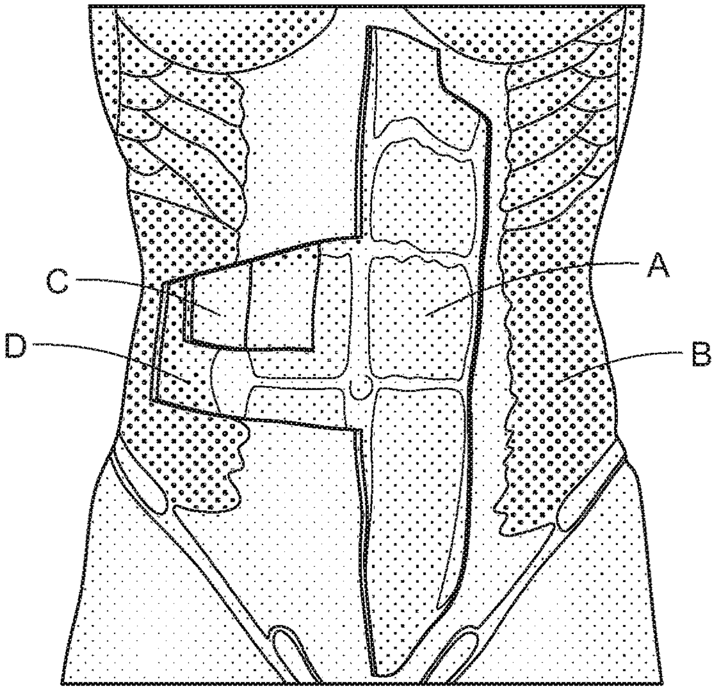
FIG. 1 illustrates the abdominal muscle anatomy illustrating A—Rectus Abdominus, B—External Oblique, C—Transverse Abdominal, and D—Internal Oblique.

It will be readily understood that the components of the embodiments, as generally described and illustrated in the figures herein, may be arranged and designed in a wide variety of different configurations in addition to the described representative embodiments. Thus, the following more detailed description of the representative embodiments, as illustrated in the figures, is not intended to limit the scope of the embodiments, as claimed, but is merely illustrative of representative embodiments.

Reference throughout this specification to "one embodiment" or "an embodiment" (or the like) means that a particular feature, structure, or characteristic described in connection with the embodiment is included in at least one embodiment. Thus, the appearance of the phrases "in one embodiment" or "in an embodiment" or the like in various places throughout this specification are not necessarily all referring to the same embodiment.

Furthermore, described features, structures, or characteristics may be combined in any suitable manner in one or more embodiments. In the following description, numerous specific details are provided to give a thorough understanding of embodiments. One skilled in the relevant art will recognize, however, that the various embodiments can be practiced without one or more of the specific details, or with other methods, components, materials, et cetera. In other instances, well known structures, materials, or operations are not shown or described in detail to avoid obfuscation.

As used herein and in the appended claims, the singular forms "a," "an", and "the" include plural references unless the context clearly dictates otherwise. Thus, for example, reference to "an extending length of tape" includes a plurality of such extending lengths of tape and equivalents thereof known to those skilled in the art, and so forth, and reference to "the extending length of tape" is a reference to one or more such extending length of tape and equivalents thereof known to those skilled in the art, and so forth. Recitation of ranges of values herein are merely intended to serve as a shorthand method of referring individually to each separate value falling within the range. Unless otherwise indicated herein, and each separate value, as well as intermediate ranges, are incorporated into the specification as if individually recited herein. All methods described herein can be performed in any suitable order unless otherwise indicated herein or otherwise clearly contraindicated by the text.

Although a number of representative embodiments hereof are discussed for use with infants, one skilled in the art will appreciate that the devices, systems, and methods hereof may also be used in connection with umbilical hernias in older children and in adults. In general, the design and functionality of the devices, systems, and method hereof differs little between use in connection with infants, children, and adult. Typically, only the size of the device or system is changed. In the case of used of the devices, systems, and method hereof in connection with adults (for example, in connection with pregnant women) the goal may often be more of maintenance (that is, preventing an umbilical hernia from worsening) rather than healing the hernia.

The devices, systems, and methods hereof provide a safe, non-surgical, prefabricated, and user/parent friendly way to improve the appearance of the belly button area and medical outcome for those with an umbilical hernia. The devices, systems, and methods hereof assist the muscles to approximate together and decrease the size of the gap between the muscles, which also may improve ability to stabilize and activate core muscles. The safe and parent- or user-friendly systems hereof can help avoid an unnecessary surgery and can result in improvement within about 30 days in the case of infants. In general, the sooner the problem is addressed, the faster the results.

The devices and system hereof help in approximating the rectus abdominal muscles to promote umbilical hernia closure, while not restricting age-appropriate belly breathing. Further, the devices and system hereof improve the overall appearance of the belly button area of the infant or toddler with an umbilical hernia. The devices and systems hereof promote proper muscle alignment to promote age-appropriate strength and development. Moreover, the devices and system hereof may be used to avoid expensive and unnecessary surgery later in life as a result of persistence of an umbilical hernia.

Figure 2:
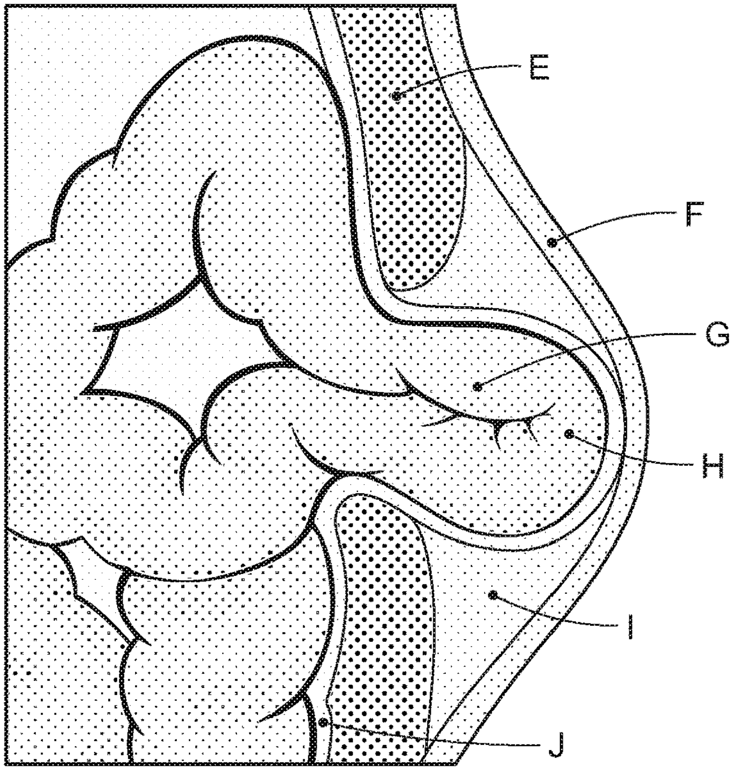
FIG. 2 illustrates an umbilical hernia, wherein E is Abdominal Muscles, F is Skin, G is Loop of intestine, H is hernia sac, I is Subcutaneous fatty tissue, and J is the Peritoneum.
Figure 3:
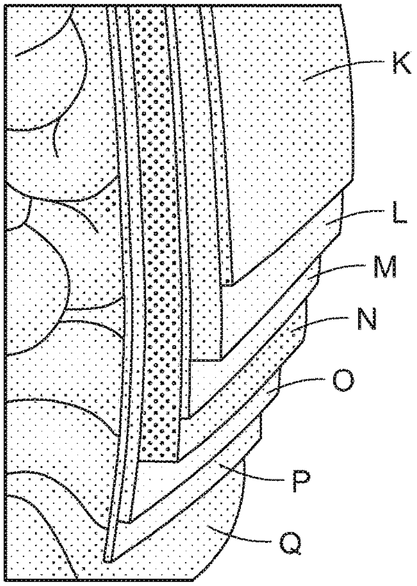
FIG. 3 illustrates the layers of tissue overlying the intestines in the abdomen wherein K is Skin, L is Fat, M is Connective tissue, N is muscle, O is Connective tissue, P is Peritoneum, and Q is Intestine.

FIG. 1 illustrates typical abdominal muscle anatomy, as seen from the frontal view. There are three main classifications of muscles that make up the core. First, the rectus abdominus run vertically alongside the umbilicus to flex the stomach as during a sit up. Second, the internal and external obliques run at opposite diagonals (like an X) towards the middle of the stomach which allow for rotation type movements of the core. Further, the transverse abdominus muscle wraps completely around the lower stomach and back to form a corset, providing stability and protection to the core. An umbilical hernia pierces through all of these muscles to create a hole where the belly button is typically located, disrupting the stability, protection, and movement functions of all of these muscles, as illustrated in FIG. 2. As a result of this weakness in the system, abdominal contents push out into the hernial sac, which is also depicted in the side view of FIG. 2. FIG. 3 illustrates the layers of tissue overlying the intestines in the area of the abdomen.

The devices and systems described herein may, for example, assist in closure of an umbilical hernia in infants and reduce discomfort from protruding hernial sac. The devices and systems hereof are non-invasive, safe, and prefabricated. The prefabricated systems and devices hereof provide a parent-friendly way to help bring the abdominal muscles together and promote self-healing of the weakened portion of the abdominal wall. The devices and systems hereof also promote the natural rhythm of the manner in which a baby belly-breathes and moves by being flexible and non-circumferential (that is, not extending around the entire waist of the child). The umbilicus is not occluded which promotes proper cleaning and aeration of the umbilical skin area. Covering the umbilicus can provide a source of infection or bacteria. In a number of embodiments, the devices and systems hereof are water resistant, so that the baby can be bathed as they normally would while still wearing the device. Furthermore, the device can be removed easily and without discomfort to the child by, for example, applying baby oil or lotion (such as typically used in infant skin care) to the area prior to removal.

An embodiment of a device or system 10 hereof suitable for use with infants, older children and, adults is illustrated in FIGS. 4A through 4D. In a number of embodiments, device 10 is formed of a therapeutic adhesive tape such as a non-latex based elastic cotton tape that is flexible. In general, the tension applied by such therapeutic tape can be adjusted by the amount or percentage of stretching during application. Device 10 includes a first section 20 having a passage or opening 22 formed therein. In a number of embodiments for use in connection with infants, first section 20 was approximately 2 inches (5.08 cm; in an unstretched state) in width and opening 22 is sufficiently wide to be able to encompass a mild to moderate hernia and associated tented skin to be treated. A plurality of extending sections or lengths of tape 30 are formed integrally with the first section 20 and extend laterally therefrom. Extending sections 30 may be applied diagonally (or extending at an angle) from first section 20. In a number of studied embodiments for use in connection with infants, extending sections 30 were approximately 1 inch (2.54 cm) in width and approximately 2 to 2.5 inches (5.08 to 6.35 cm; in an unstretched state) in length.

In a number of embodiments, extending sections 30 can range 0.5 inches (1.27 cm) and 1 inch (2.54 cm) in width. Based on clinical experience, irritation to the skin typically increases with increasing tape width. However, tape having a width less than 0.5 inch (1.27 cm) typically become very difficult to use and often become twisted on itself.

The material properties of such tapes are, for example, described in Boonkerd, C. and Limroongreungrat, W., Elastic therapeutic tape: do they have the same material properties?, J. Phys. Ther. Sci. 28:1303-1306, 2016, the disclosure of which is incorporated herein by reference. Elastic therapeutic tapes such as used in extending sections 30 typically provide a maximum elongation in the range of approximately 50 to 150%.

In a number of embodiments, the elasticity of first section 20 of adhesive elastic tape is less than the elasticity of extending sections 30 and first section 20 is more difficult to stretch than extending sections 30. In a number of embodiments, first section 20, which is positioned around the navel upon application, is thicker and/or provides less elasticity/stretchability of the tape itself. For example, first section 20 may be formed from a double layer of the tape (for example, kinesiology tape) that is used in forming extending sections 30. Additionally or alternatively, one may make first section 20 longer and/or apply an elastic layer thereto by spraying, stamping, or painting. For example, a layer of silicon or other elastic material can be applied over the area of first section 20. In general, the components of the first section are integrally formed at the time of manufacture. First section 20 may, for example, be 15% to 85% less elastic or stretchable than extending sections 30. The properties of first section 20 assist in the application of device 10 and to provide the stability needed to approximate the left and right rectus abdominis muscles. Such properties reduce the difficulty in applying device 10 to help enable parents (or other users) to apply device 10 without the assistance of a therapist in applying the varied tension of the adhesive tape of device 10 in a manner that is optimal to achieve the best results. The varied tension is built into device 10.

In a number of studied embodiments in which extending sections 30 were approximately 2 inches (5.08 cm) in length, the maximum stretched length of extending sections 30 was approximately 8 cm, providing a maximum elongation of 60%. First section 20 had an initial length of approximately 5.08 cm and exhibited a maximum stretched length of 7 cm, corresponding to a maximum elongation of 40%. In the studied embodiments, each of extending sections 30 were formed from a single, continuous layer of therapeutic adhesive tape, and first section 20 included a second layer of the therapeutic adhesive tape used in extending sections 30 and overlaid upon the layer of therapeutic tape forming extending sections 30. The two layers of therapeutic adhesive tape of first section 20 were oriented in a parallel (fiber) direction. If the second layer of first section 20 were oriented perpendicular to the first layer, the elasticity would be even further reduce (potentially to approximately 0). However, if the fibers of the tape are aligned in a cross or perpendicular pattern, air flow may be reduced excessively. Moreover, it is desirable to provide some elasticity in first section 20. Once again, however, the elasticity (maximum elongation) of first section 20 should be reduced compared extending sections 30.

The elastic properties of the lateral/diagonal extending sections 30 of adhesive tape provide more elasticity or stretchability as described above. The increased stretchability extending sections 30 of device 10 promotes muscle activation of the oblique and transverse abdominus muscle fibers by their connection to the skin via fascial layers (see FIG. 3) and gentle gliding of those layers as the infant moves and contracts his or her muscles naturally. Device 10 is non-invasive and is not chemically or electrically stimulating the muscles.

Figure 4A:
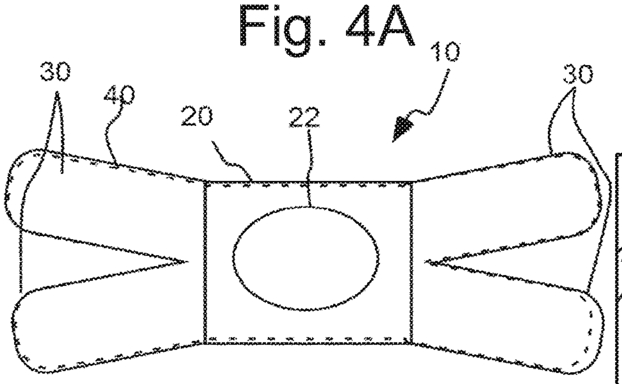
FIG. 4A illustrates a top plan view of an embodiment of a device or system.
Figure 4B:
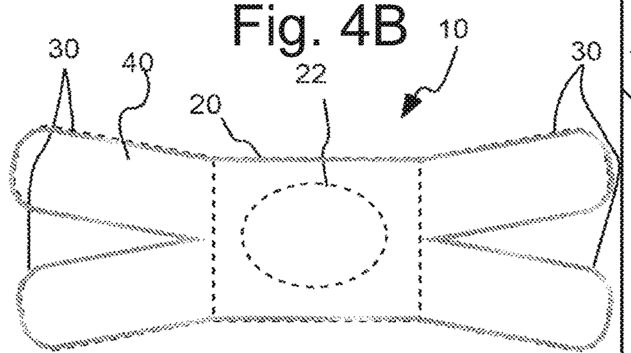
FIG. 4B illustrates a bottom plan view of the embodiment of FIG. 4A with extending sections extending from the first section at an angle.
Figure 4C:
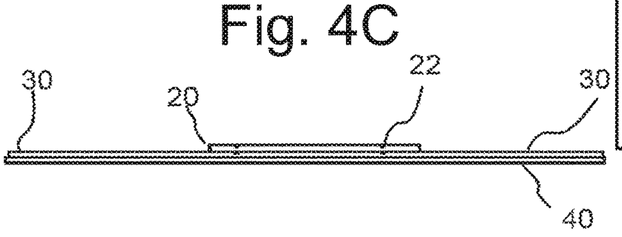
FIG. 4C illustrates a side view of the embodiment of FIG. 4A.
Figure 4D:
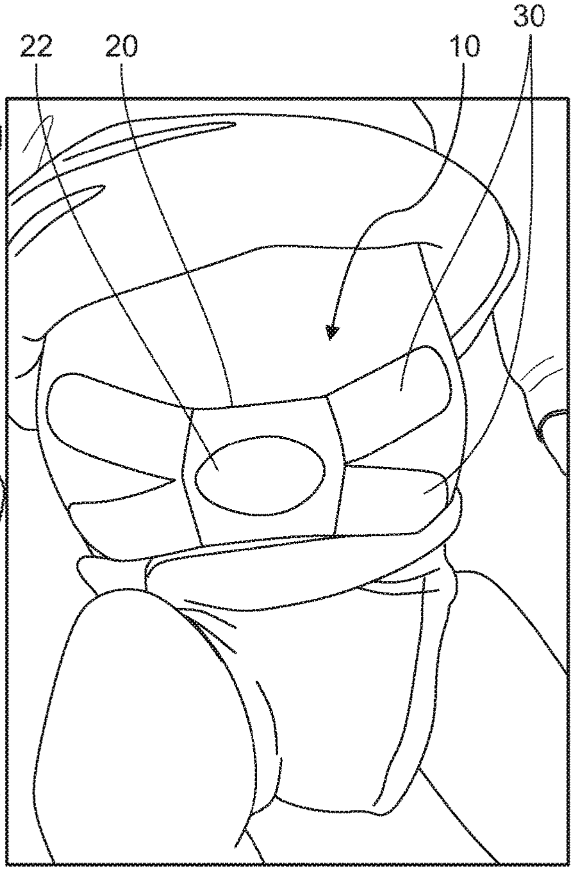
FIG. 4D illustrates an embodiment of the device or system of FIG. 4A applied to an infant's abdomen.

To apply device 10, one or more sections of paper backing or backing layer(s) 40 (see FIGS. 4A through 4C and 5), which covers and protects an adhesive layer, is/are first removed in the intermediately positioned first section 20, and first section 20 is applied gently around the herniated area. Then, paper backing 40 can be removed from each extending section 30, and each extending section 30 can be applied at a variety of angles (relative to first section 20, which are adjustable upon application) to promote activation of the lateral trunk muscles (internal and external obliques). Extending sections 30 may be applied gently with little to no stretching of tape needed during the application. Clinically, in a number of embodiments, a 10-20% stretch of each of first section 20 and extending sections 30 is suitable. This application method will allow the tape to stretch with the infant as it moves and breathes. The flexibility of the adhesive tape material allows extending sections 30 to be placed in a variety of functional positions and to decrease any potential skin irritation (via positional variation) with continued use. Device 10 is illustrated in FIG. 4D applied to a three-month old infant with an umbilical hernia ($1^{st}$ application). In the illustrated embodiment, two laterally/diagonally extending sections 30 are provided on each side of first section 20. However, the number of extending sections 30 on each side may vary independently. In a number of embodiments, two to four extending sections 30 are provided on each side of first section 20.

Figures 5, 6:
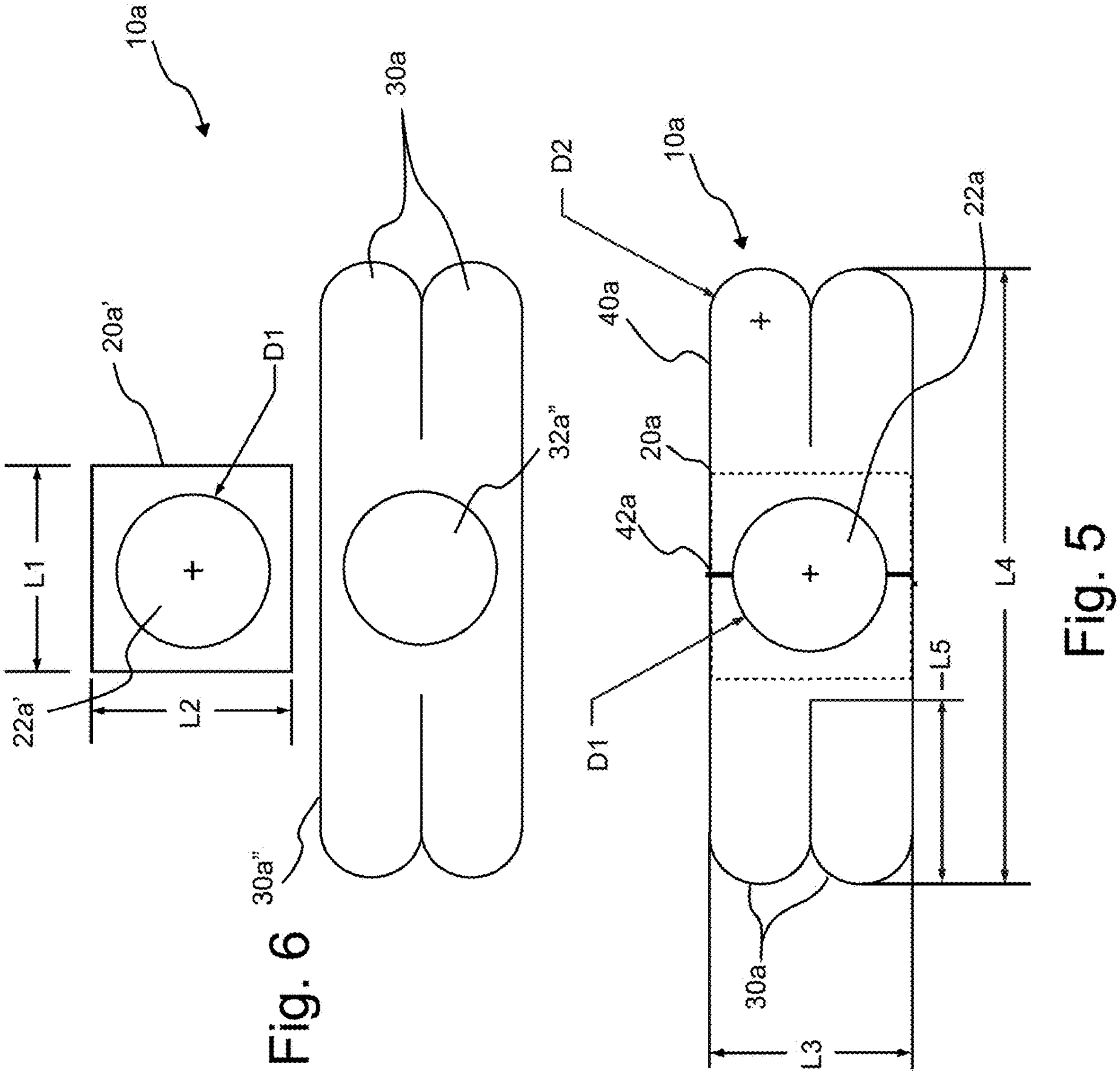
FIG. 5 illustrates a bottom plan view of an embodiment of a device or system hereof; wherein representative dimensions, in inches, are: L3=2.00, L4=6.00, L5=1.75 (slit width, both sides), and D1=1.00 (diameter on center).
FIG. 6 illustrates a top plan view of the device of FIG. 5 in a disconnected or disassembled state; wherein representative dimensions, in inches, are: L1=2.00, L2=2.00, D1 is 1.00 and D2=1.00 (diameter on center, four places).

In the embodiment illustrated in FIG. 5, paper backing or backing layer 40*a* of device 10*a* is formed in two sections with a slit 42*a* positioned under first section 20*a* (illustrated in dashed lines in FIG. 5) and separating backing layer 40*a* into two backing layer sections. During application, the person applying device 10*a* can peel backing layer 40*a* from underneath first section 20*a* and apply that portion of device 10*a* to the patient with opening 22*a* positioned around the umbilical hernia. The remainder of each section of backing layer 40*a* can then be removed to adhere extending sections 30*a* to the patient. In other embodiments, two slits are provided in a paper backing or backing layer, wherein one slit is positioned on each side of opening 22*a*. Such slits may, for example, be positioned laterally at the approximate position wherein extending sections 30 meet first section 20.

FIG. 6 illustrates device 10*a* of FIG. 5 in a disassembled state showing a bottom layer 30*a*" of flexible and elastic adhesive tape material. Bottom layer 30*a*" includes extending sections 30*a* and a generally central opening 32*a*". Device 10*a* further includes a top layer 20*a*' of flexible and elastic adhesive tape material (which can be the same type of flexible and adhesive tape material used in bottom layer 30*a*"). Top layer 20*a*' includes an opening 22*a*'. Top layer 20*a*' is overlayed upon first layer 30*a* to form first section 20*a* of device 10*a*. During assembly, opening 22*a*' is aligned with opening 32*a*" to from opening 42*a* of device 10*a*.

Figure 7A:
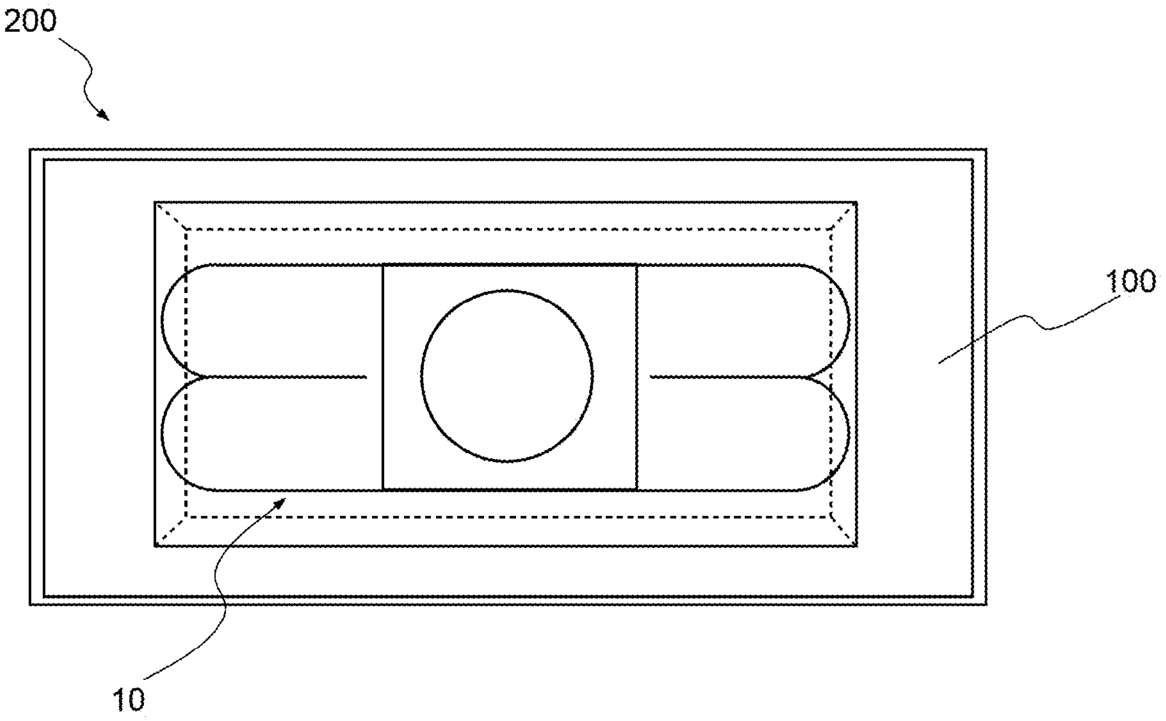
FIG. 7A illustrates a top plan view of a kit including a plurality of devices hereof within packaging.
Figure 7B:
FIG. 7B illustrates a side view of the kit of FIG. 7A.

As illustrated in the embodiment of FIGS. 7A and 7B, devices 10, 10*a* or other devices hereof may, for example, be provided in a kit 200 including a plurality of such devices 10, 10*a* within a packaging system 100 (as known in the packaging arts). Devices hereof may, for example, be applied for a period of several days and then removed. For example, in a number of embodiments, devices hereof may remain on the child (or adult patient) for up to three days, and then will be reapplied after 24 hours of non-use to allow the skin to breathe. A new device hereof may be reapplied in this manner until closure of the hernia is achieved.

A good portion of umbilical hernias either require surgical closure after the age of 3 or some will close on their own. The devices, systems, and methods hereof can promote umbilical hernia closure within 30-60 days, if applied to a young infant. Older children will still see improvements, but such improvements may take longer. As described above, adults may benefit from use of the devices, systems, and method hereof in improving or preventing/limiting worsening of umbilical hernias. The devices, systems, and methods hereof provide parents and other users with a safe, non-invasive way to help improve the outcomes of an umbilical hernia by muscle approximation and activation support, in significantly less time than the traditional "wait and see" approach used with infants, while still promoting proper hygiene and breathing mechanics.

The foregoing description and accompanying drawings set forth a number of representative embodiments at the present time. Various modifications, additions and alternative designs will, of course, become apparent to those skilled in the art in light of the foregoing teachings without departing from the scope hereof, which is indicated by the following claims rather than by the foregoing description. All changes and variations that fall within the meaning and range of equivalency of the claims are to be embraced within their scope.

What is claimed is:

1. A device for treatment of an umbilical hernia of an infant or toddler, comprising:

a first section of flexible, elastic material comprising an adhesive layer on a rearward side thereof, the first section comprising an opening therein dimensioned to be sufficiently large such that the circumference of the opening is positionable around the umbilical hernia and is configured such that the umbilicus is not occluded and open to environmental air, and a plurality of extending sections of flexible, elastic material attached to and extending from the first section, each of the plurality of extending sections comprising an adhesive layer on a rearward side thereof, wherein the first section requires greater force to stretch than each of the plurality of extending sections, wherein the device is configured to approximate rectus abdominus muscles of the infant or toddler when positioned around the umbilical hernia to promote closure of the umbilical hernia.

2. The device of claim 1 wherein a first plurality of the extending sections extend from a first side of the first section and a second plurality of the extending sections extend from a second side of the first section.

3. The device of claim 2 wherein the first plurality of extending sections and the second plurality of extending sections have a maximum elongation in the range of 25 to 150%.

4. The device of claim 2 wherein the first plurality of extending sections and the second plurality of extending sections have a maximum elongation in the range of 25 to 100%.

5. The device of claim 2 wherein the first plurality of extending sections and the second plurality of extending sections have a maximum elongation in the range of 50 to 100%.

6. The device of claim 1 further comprising one or more removable backing sections over the adhesive layer of the first section and the adhesive layer of each of the plurality of extending sections.

7. The device of claim 1 wherein a maximum elongation of the first section is in the range of 15 to 85% less than a maximum elongation of the plurality of extending sections.

8. The device of claim 1 wherein a portion of the first section which is configured to be in contact with skin of the infant or the toddler upon application of the device has a thickness greater than each of the plurality of extending sections.

9. A method of treating an umbilical hernia of an infant or a toddler, comprising:

applying a preassembled device to the abdomen of the infant or the toddler, the preassembled device comprising a first section of flexible, elastic material comprising an adhesive layer on a rearward side thereof, the first section comprising an opening therein, and a plurality of extending sections of flexible, elastic material attached to and extending from the first section, each of the plurality of extending sections comprising an adhesive layer on a rearward side thereof, wherein applying the preassembled device comprises applying the first section to the abdomen of the infant or toddler via the adhesive layer thereof so that a circumference of the opening is positioned around the umbilical hernia and the umbilicus is not occluded, and applying each of the plurality of extending sections to the abdomen via the adhesive layer thereof in an extended state, and wherein the first section requires greater force to stretch than each of the plurality of extending sections such that the device is configured to approximate rectus abdominus muscles of the infant or toddler when positioned around the umbilical hernia to promote closure of the umbilical hernia.

10. The method of claim 9 wherein a first plurality of the extending sections extend from a first side of the first section and a second plurality of the extending sections extend from a second side of the first section.

11. The method of claim 10 wherein the first plurality of extending sections and the second plurality of extending sections have a maximum elongation in the range of 25 to 150%.

12. The method of claim 10 wherein the first plurality of extending sections and the second plurality of extending sections have a maximum elongation in the range of 50 to 100%.

13. The method of claim 9 wherein the preassembled device includes one or more removable backing sections over the adhesive layer of the first section and the adhesive layer of each of the plurality of extending sections, and the method further comprises removing the one or more removable backing sections over the adhesive layer of the first section and over the plurality of extending sections before application of the first section and the plurality of extending sections.

14. The method of claim 9 wherein the opening has a diameter of at least one inch in an unstretched state before application.

15. The method of claim 9 wherein a maximum elongation of the first section is in the range of 15 to 85% less than a maximum elongation of the plurality of extending sections.

16. A kit, comprising: a plurality of devices for treatment of an umbilical hernia in an infant or toddler which are prefabricated for application, each of the devices comprising a first section of flexible, elastic material comprising an adhesive layer on a rearward side thereof, the first section comprising an opening therein dimensioned to be sufficiently large such that the circumference of the opening is positionable on the abdomen of the infant or toddler, around the umbilical hernia, and is configured such that the umbilicus is not occluded, and a plurality of extending sections of flexible, elastic material attached to and extending from the first section, each of the plurality of extending sections comprising an adhesive layer on a rearward side thereof for attachment to the abdomen of the infant or toddler, wherein the first section requires greater force to stretch than each of the plurality of extending sections and the device is configured to approximate rectus abdominus muscles of the infant or toddler when positioned on the abdomen, to promote closure of the umbilical hernia.

17. The kit of claim 16 wherein a first plurality of extending sections extend from a first side of the first section and a second plurality of the extending sections extend from a second side of the first section.

18. The kit of claim 17 wherein each of the first plurality of extending sections and each of the second plurality of extending sections of each device has a maximum elongation in the range of 25 to 150%.

19. The kit of claim 16 wherein a maximum elongation of the first section is in the range of 15 to 85% less than a maximum elongation of the plurality of extending sections.

20. The kit of claim 16 wherein a portion of the first section of each of the plurality of devices which is configured to be in contact with skin of the infant or the toddler upon application of the device has a thickness greater than each of the plurality of extending sections.

* * * * *